(12) United States Patent  (10) Patent No.: US 8,031,340 B2
Rich et al. (45) Date of Patent: Oct. 4, 2011

(54) OPTICAL SYSTEM FOR A FLOW CYTOMETER

(75) Inventors: Collin A. Rich, Ypsilanti, MI (US); Nathaniel C. Bair, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 0 days.

(21) Appl. No.: 12/887,392

(22) Filed: Sep. 21, 2010

(65) Prior Publication Data
US 2011/0058168 A1 Mar. 10, 2011

Related U.S. Application Data

(63) Continuation-in-part of application No. 12/197,192, filed on Aug. 22, 2008, which is a continuation-in-part of application No. PCT/US07/04836, filed on Feb. 22, 2007.

(60) Provisional application No. 61/014,382, filed on Dec. 17, 2007, provisional application No. 61/014,425, filed on Dec. 17, 2007, provisional application No. 61/018,233, filed on Dec. 31, 2007, provisional application No. 60/776,125, filed on Feb. 22, 2006.

(51) Int. Cl.
*G01N 21/00* (2006.01)

(52) U.S. Cl. ........ 356/343; 356/338; 356/311; 356/318; 422/73; 422/82.08; 422/82.05; 436/55; 436/36; 436/164

(58) Field of Classification Search .......... 356/338–343, 356/311–318; 422/73, 67, 82.08, 82.05; 436/36, 55, 54, 164
See application file for complete search history.

(56) References Cited

U.S. PATENT DOCUMENTS

| 4,933,813 | A | 6/1990 | Berger |
| 5,028,127 | A | 7/1991 | Spitzberg |
| 5,139,609 | A | 8/1992 | Fields et al. |
| 5,739,902 | A | 4/1998 | Gjelsnes et al. |
| 5,798,222 | A | 8/1998 | Goix |

(Continued)

FOREIGN PATENT DOCUMENTS
EP 1396736 A2 3/2004
(Continued)

OTHER PUBLICATIONS
U.S. Appl. No. 12/939,836, filed Nov. 4, 2010, Rich.

*Primary Examiner* — Gregory J Toatley
*Assistant Examiner* — Iyabo S Alli
(74) *Attorney, Agent, or Firm* — Jeffrey Schox

(57) ABSTRACT

An optical system for a flow cytometer having a flow channel with an interrogation zone and an illumination source that impinges the flow channel in the interrogation zone includes a lens system and a detection system. The lens system preferably includes at least two lens surfaces located on opposite sides of the flow channel and configured to collect and collimate light from the interrogation zone. The detection system, configured to detect light from the lens system, preferably includes first and second detectors, a first filter that passes a first wavelength of light and reflects a second wavelength of light, and a second filter that reflects the first wavelength of light and passes the second wavelength of light, wherein the first and second filters are aligned such that light reflected from the first filter passes into the second detector and light reflected from the second filter passes into the first detector.

24 Claims, 8 Drawing Sheets

U.S. PATENT DOCUMENTS

| | | | |
|---|---|---|---|
| 6,016,376 | A | 1/2000 | Ghaemi et al. |
| 6,067,157 | A | 5/2000 | Altendorf |
| 6,091,502 | A | 7/2000 | Weigl et al. |
| 6,097,485 | A | 8/2000 | Lievan |
| 6,154,276 | A | 11/2000 | Mariella, Jr. |
| 6,377,721 | B1 | 4/2002 | Walt et al. |
| 6,403,378 | B1 | 6/2002 | Phi-Wilson et al. |
| 6,469,787 | B1 | 10/2002 | Meyer et al. |
| 6,519,355 | B2 | 2/2003 | Nelson |
| 6,522,775 | B2 | 2/2003 | Nelson |
| 6,636,623 | B2 | 10/2003 | Nelson et al. |
| 6,700,130 | B2 | 3/2004 | Fritz |
| 6,859,570 | B2 | 2/2005 | Walt et al. |
| 6,869,569 | B2 | 3/2005 | Kramer |
| 6,936,828 | B2 | 8/2005 | Saccomanno |
| 6,944,322 | B2 | 9/2005 | Johnson et al. |
| 7,009,189 | B2 | 3/2006 | Saccomanno |
| 7,012,689 | B2 | 3/2006 | Sharpe |
| 7,075,647 | B2 | 7/2006 | Christodoulou |
| 7,113,266 | B1 | 9/2006 | Wells |
| 7,232,687 | B2 | 6/2007 | Lary et al. |
| 7,262,838 | B2 | 8/2007 | Fritz |
| 7,471,393 | B2 * | 12/2008 | Trainer .................. 356/336 |
| 7,738,099 | B2 * | 6/2010 | Morrell et al. ............ 356/343 |
| 7,843,561 | B2 | 11/2010 | Rich |
| 2004/0048362 | A1 | 3/2004 | Trulson et al. |
| 2004/0175837 | A1 | 9/2004 | Bonne et al. |
| 2004/0201845 | A1 | 10/2004 | Quist et al. |
| 2005/0047292 | A1 | 3/2005 | Park et al. |
| 2005/0057749 | A1 | 3/2005 | Dietz et al. |
| 2005/0078299 | A1 | 4/2005 | Fritz et al. |
| 2005/0105091 | A1 | 5/2005 | Lieberman et al. |
| 2005/0162648 | A1 | 7/2005 | Auer et al. |
| 2005/0163663 | A1 | 7/2005 | Martino et al. |
| 2005/0195605 | A1 | 9/2005 | Saccomanno et al. |
| 2006/0002634 | A1 | 1/2006 | Riley |
| 2006/0023219 | A1 | 2/2006 | Meyer et al. |
| 2006/0281143 | A1 | 12/2006 | Liu et al. |
| 2007/0041013 | A1 | 2/2007 | Fritz et al. |
| 2007/0096039 | A1 | 5/2007 | Kapoor et al. |
| 2008/0064113 | A1 | 3/2008 | Goix et al. |
| 2009/0174881 | A1 | 7/2009 | Rich |
| 2011/0058163 | A1 | 3/2011 | Rich |

FOREIGN PATENT DOCUMENTS

| | | |
|---|---|---|
| WO | 2005/073694 | 1/2005 |
| WO | 2007/100723 | 2/2007 |
| WO | 2008/058217 | 11/2007 |

\* cited by examiner

--- WAVELENGTH 1
— WAVELENGTH 2

← DIRECTION OF LIGHT TRAVEL

OPTICAL SYSTEM FOR A FLOW CYTOMETER

CROSS-REFERENCE TO RELATED APPLICATIONS

This application is a continuation in part of prior U.S. application Ser. No. 12/197,192 filed 22 Aug. 2008, which is a continuation in part of international application number PCT/US07/04836 filed 22 Feb. 2007, which claims priority to U.S. Provisional Application No. 60/776,125, filed 22 Feb. 2006. U.S. application Ser. No. 12/197,192 also claims the benefit of U.S. Provisional Application No. 61/014,382 filed 17 Dec. 2007, U.S. Provisional Application No. 61/014,425 filed 17 Dec. 2007, and U.S. Provisional Application No. 61/018,233 filed 31 Dec. 2007. All six patent documents (one U.S. application, one international patent application, and the four U.S. Provisional Applications) are incorporated in their entirety by this reference.

TECHNICAL FIELD

This invention relates generally to the flow cytometer field, and more specifically to a new and useful optical system in the flow cytometry field.

BACKGROUND

The conventional optical system for flow cytometers includes a collecting lens to collect light from the interrogation zone, beam splitters to split the light into different channels based on wavelength, and several detector subsystems with filters to pass only particular wavelengths (such as 515-545 nm, 564-606 nm, and 653-669 nm).

To use the conventional optical system, the beam splitters and filters must be arranged in a very particular order (monotonically increasing or decreasing order). For example, a first beam splitter must split between the two lower frequency bands, a first detector subsystem must filter between the lowest frequency band, a second beam splitter must split between the two higher frequency bands, a second detector subsystem must filter between the middle frequency bands, and a third detector subsystem must filter between the highest frequency bands. To change the wavelength detection of the conventional optical system (for example, to replace the frequency band that is originally the highest with a frequency band that is now the lowest) would require the re-arrangement of the entire optical system (including swapping both filters and beam splitters). In other words, with a conventional optical system, the step of filtering the light of the first channel affects the light of the second channel.

Thus, the user must skillfully arrange the filters in a particular order or the detector subsystems will not function correctly. This limitation prevents the easy swapability of the filters and the easy modification of detection parameters. Further, the particular arrangement of the optical table decreases the reliability and the ruggedness of the flow cytometer since the alignment of the beam splitters affects the detection of each of the detector subsystems.

Thus, there is a need in the flow cytometer field to create a new and useful optical system. This invention provides such new and useful optical system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. The Optical System

Figure 1:
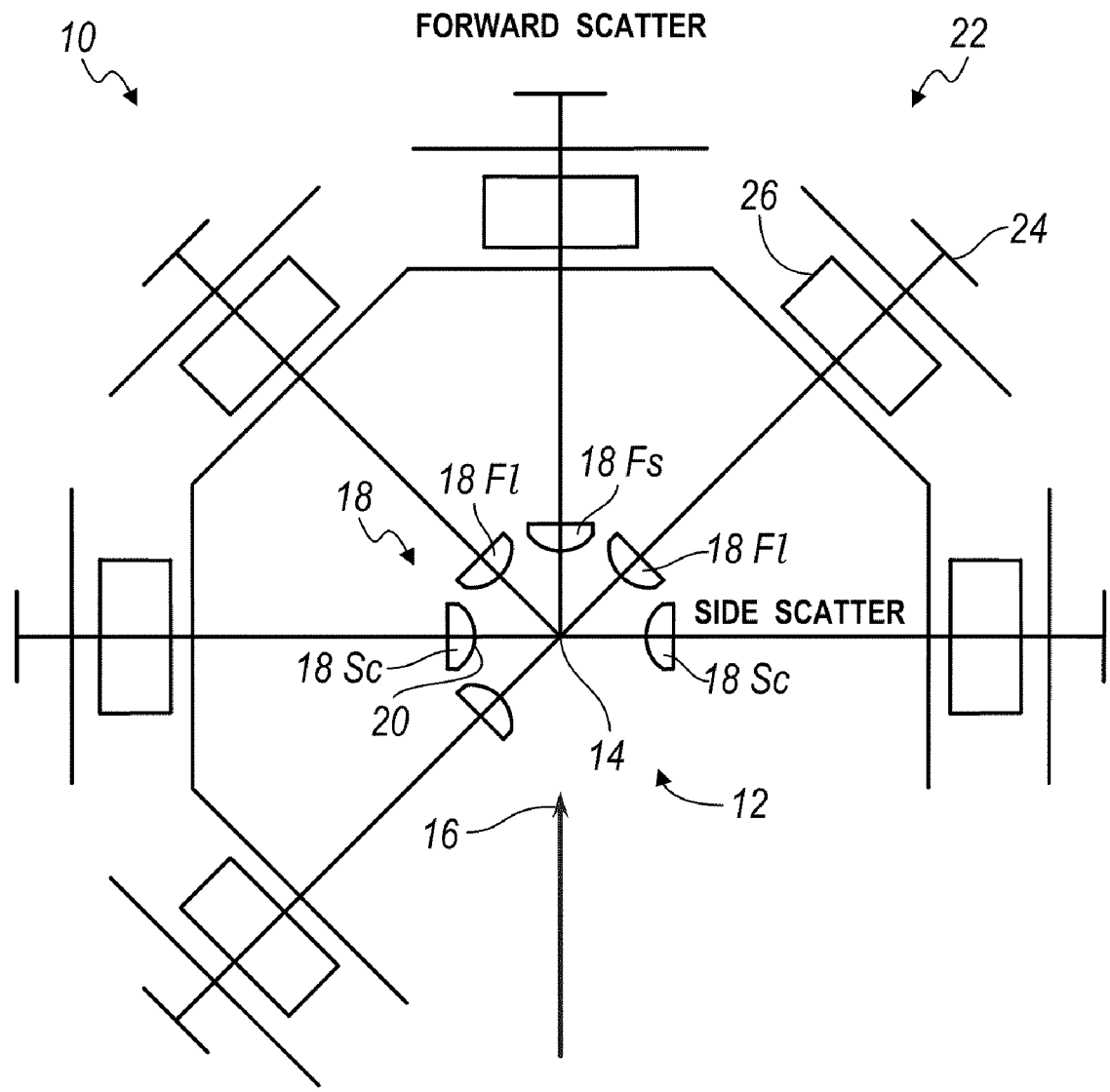
FIG. 1 is a schematic representation of the preferred embodiment of the invention.

As shown in FIG. 1, the optical system 10 of the preferred embodiments of the invention is preferably integrated into a flow cytometer. In this preferred environment, the flow cytometer defines a flow channel 14 with an interrogation zone 12 and includes an illumination source 16 that impinges the interrogation zone 12 from a particular direction. The optical system 10 preferably includes a lens system 18 with multiple lens surfaces 20 arranged around the interrogation zone 12, and a detection system 22 with multiple detectors 24 arranged to detect the light collected and collimated by the lens system 18. The multiple detectors 24 are each coupled to a local filter 26 that independently filters the collected light for specific wavelengths. Although the optical system 10 of the preferred embodiment has been specifically designed for an interrogation zone 12 of a flow cytometer, the system may alternatively be used in any suitable system to collect light along multiple paths from a single point.

The lens system 18 of the preferred embodiment functions to collect and collimate the scattered and/or emitted light from the interrogation zone 12. Preferably, the lens system 18 includes at least three lens surfaces 20 (one forward scatter, one side scatter, and one florescence). More preferably, the lens system 18 includes five or more lens surfaces 20 (one forward, two side scatter, and two or more florescence). In the preferred version, the lens system 18 is composed of separate lenses. In an alternative version, the lens system 18 may be formed as a unitary piece with multiple facets. The lens system 18 is preferably arranged along a plane parallel to the light source and perpendicular to the flow channel 14, but—as discussed in Section Two—may alternatively be arranged in any suitable manner.

Figure 2:
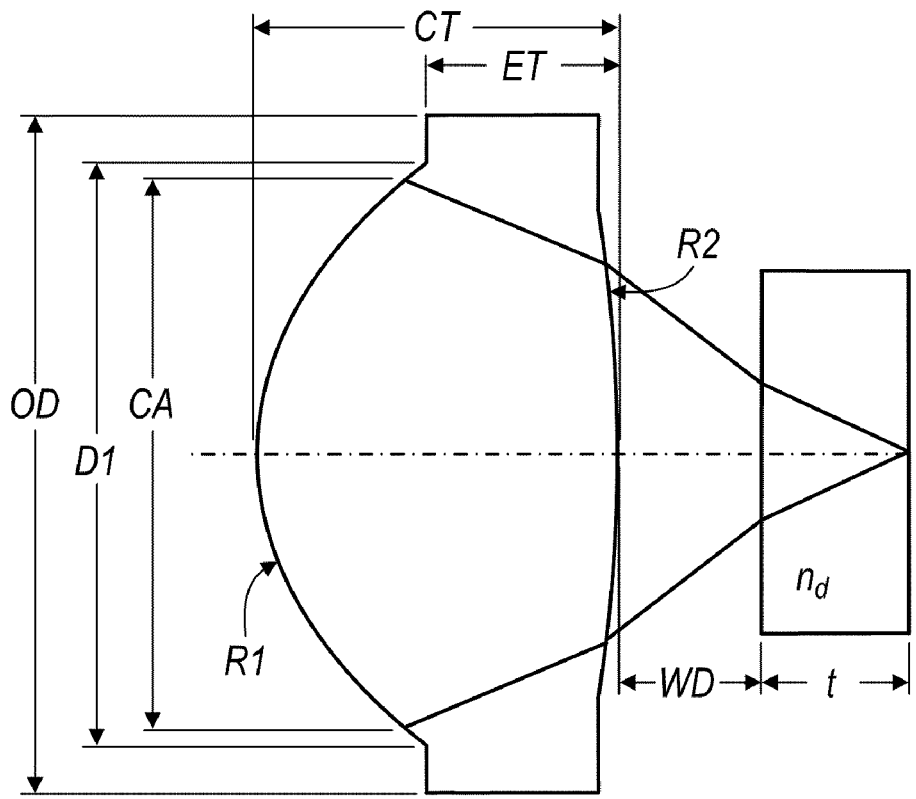
FIGS. 2 and 3 are detailed side and front views, respectively, of a collecting lens of a variation of the preferred embodiment.
Figure 3:
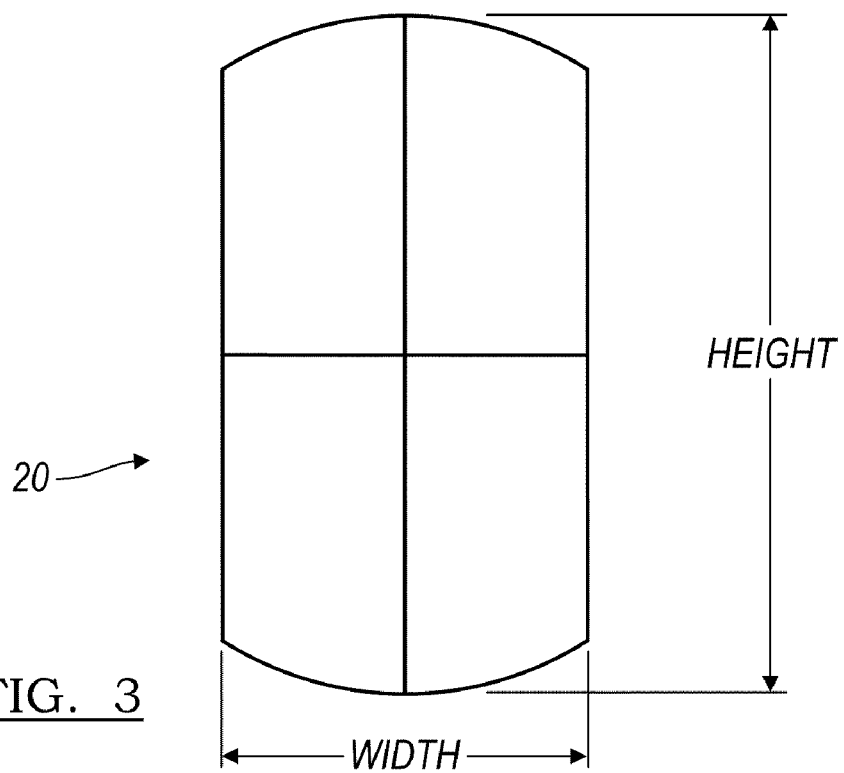

In a first variation, as shown in FIG. 1, the lens system 18 includes at least three whole lenses (preferably a 011-0330 spherical lens sourced from Optosigma of Santa Ana, Calif.). The whole lenses preferably include a usable numerical aperture of approximately 0.31. In a second variation, as shown in FIG. 2, the lens system 18 includes at least three truncated lenses (preferably a 46-347 aspherical lens sourced from Edmund Optics of Barrington, N.J.). In other variations, the lenses may be whole or truncated, may be spherical or aspherical, and may be similar or dissimilar to each other. The truncation of the lenses functions to increase the light collecting ability of the lens system 18, while maintaining a close proximity to the interrogation zone. There is a limit to the maximum size of the lens's numerical aperture due to the geometrical arrangement of the lenses around the interrogation zone 12. By truncating the lenses, they may be located the same distance from the interrogation zone 12 as a spherical lens, while having an increased height and therefore, an increased numerical aperture. With an increased light collecting ability (or increased numerical aperture of the lens surface), the system will be able to provide a brighter image and allow for the visualization of finer details. Preferably, the lenses are truncated to remove the edge of the lens. More preferably, as shown in FIGS. 2 and 3, the lenses are truncated approximately 35% in the horizontal direction to remove both the edge and a portion of the lens within the clear aperture diameter. The lenses may, however, may be truncated by any suitable amount to increase the light collecting ability of the lens system 18, while maintaining a close proximity to the interrogation zone. The width of the lens is the dimension in the plane of FIGS. 1 and 2. The numerical aperture of the lens can be increased by increasing the height of the lens. The power collection efficiency of the lens increases proportionally with the increase in height. The truncated aspherical lenses preferably include a usable numerical aperture of approximately 0.49.

The lens surfaces 20 may include coatings that function to convert the lens surfaces 20 to wavelength specific filters. The coatings may include various inorganic or organic compounds such that the compounds absorb specific wavelengths of light while transmitting other wavelengths. Each lens preferably has a different coating, such that it will filter a specific wavelength that is different from the wavelengths filtered by the other lens surfaces 20. Alternatively at least two lens surfaces 20 may have the same coating. The coated lens surfaces 20 may work cooperatively with the local filters 26 coupled to the detectors 24 that filter specific wavelengths, or may independently filter specific wavelengths.

The detector system of the preferred embodiment functions to detect light from the lens system 18. The detector system preferably includes multiple detectors 24. The detectors are preferably a photomultiplier tube ("PMT") or a photodiode, but may alternatively include any suitable device, such as a camera, to detect light or other electromagnetic energy. In the preferred embodiment, the detector system includes a detector 24 for every lens surface 20 of the lens system 18. The detectors 24 are preferably arranged in a direct path from the lens surfaces 20, and the light collected and directed by the lens system 18 is preferably guided to the detectors 24 by an appropriate light path. The light path is preferably an air channel for simplicity, but may alternatively be a fiber optic cable or any other appropriate waveguide.

The detectors 24 of the preferred embodiment are each coupled to a local filter 26 that independently filters for specific wavelengths. The local filter 26 is preferably easily accessed by the user, such that the user may swap in different filter and change the wavelength detection of the detector system. The step of filtering the light of the first channel preferably does not affect the light of the second channel of the detector system. Thus, the user may easily swap the filters in any order to achieve the same detection parameters. Further, since the each of the detectors is independently aligned with the local filter and the lens surface, the optic system experiences increased reliability and the ruggedness over conventional flow cytometers.

2. The Arrangement of the Lens and Detector Systems

Figure 4:
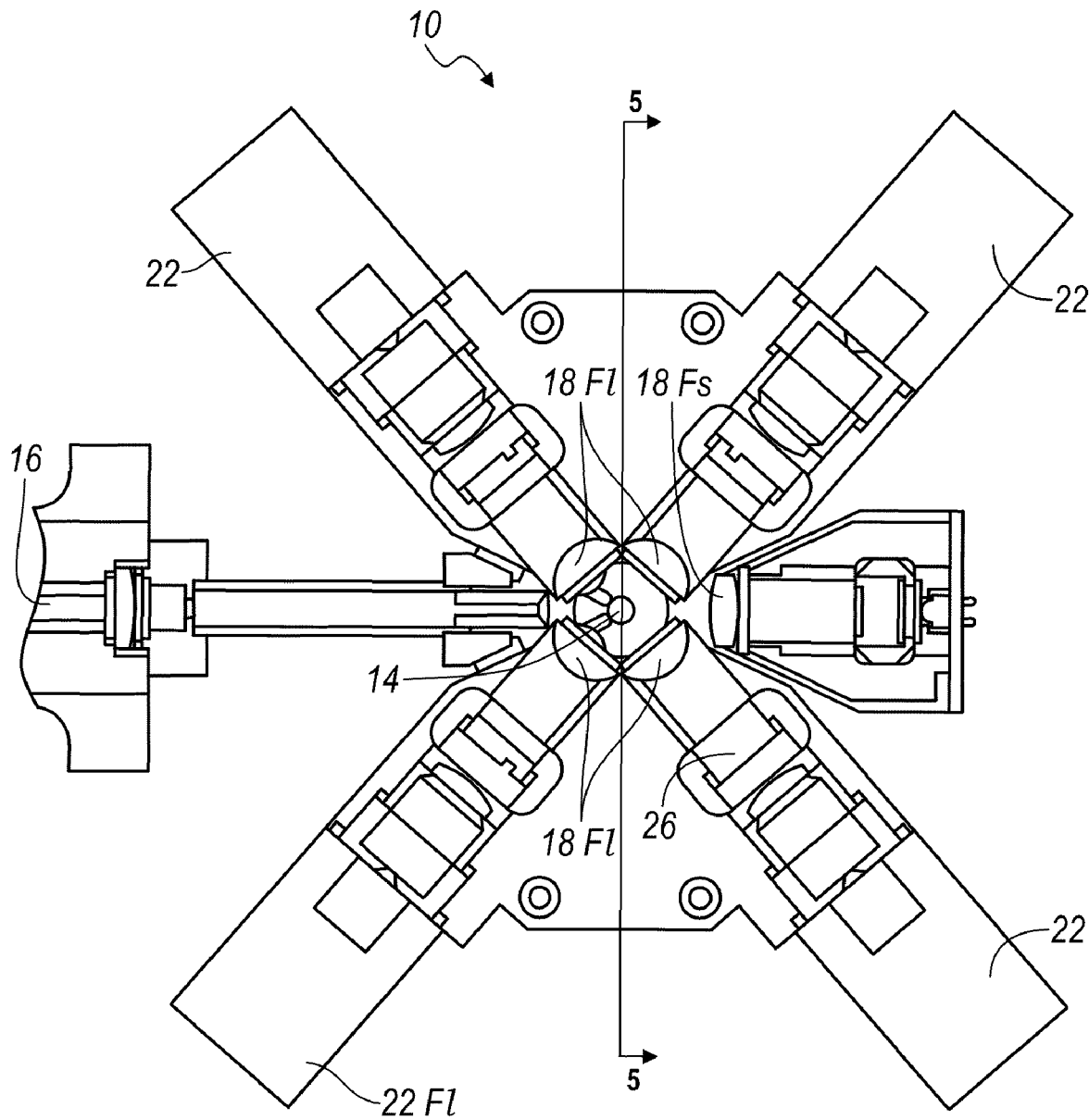
FIGS. 4 and 5 are horizontal and vertical cross sections, respectively, of a first variation of the lens and detector system arrangement of the preferred embodiment.
Figure 5:
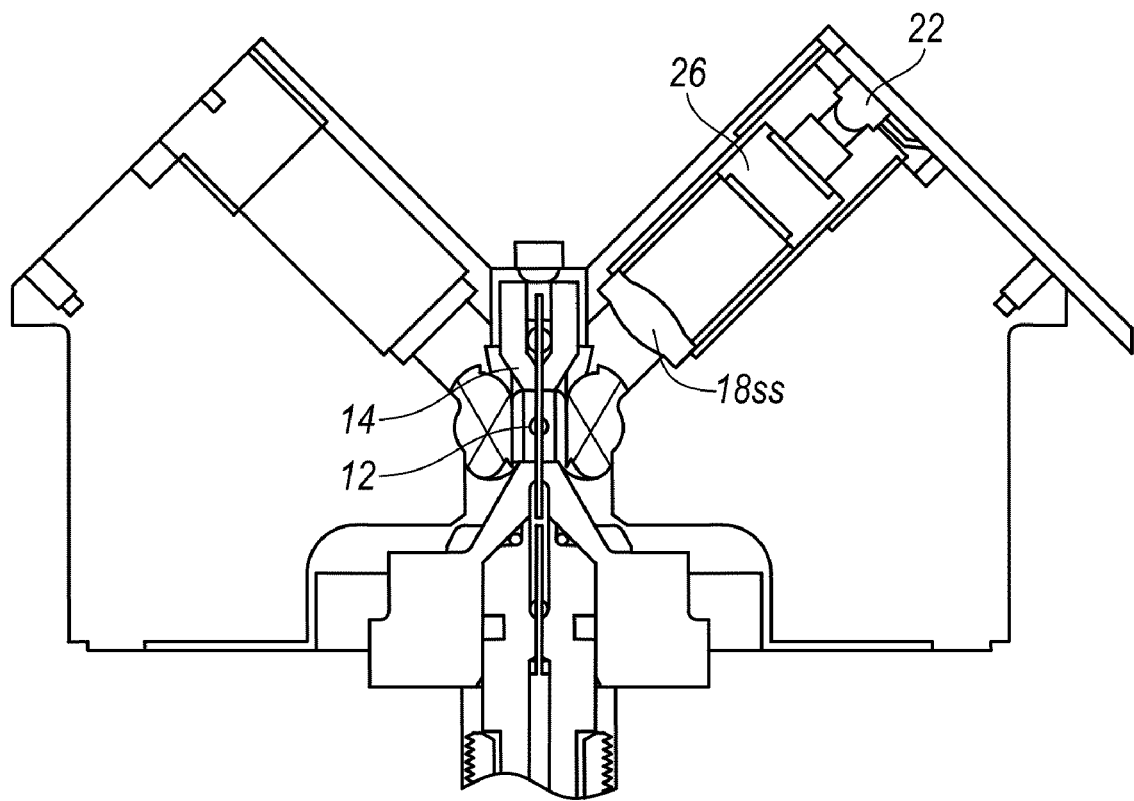

As shown in FIGS. 1 and 4-6, the lens system 18 preferably includes at least two lenses 18ss that function to collect side scatter from the interrogation zone of the flow channel, at least two lenses 18fl that function to collect fluorescence from the interrogation zone of the flow channel, and one lens 18fs that functions to collect forward scatter from the interrogation zone of the flow channel. In a first version, as shown in FIG. 1, all of the lenses are arranged in a common plane. In a second version, as shown in FIGS. 4 and 5, the lenses 18fl and 18fs adapted to collect the fluorescence and forward scatter are arranged in a common plane, while the lenses 18ss adapted to collect the side scatter are arranged in a different plane. By moving at least one of the lenses outside of the plane (and thereby reducing number of lenses in the lens system 18 in the plane perpendicular to the flow channel 14), the lenses may be arranged in a more compact configuration around the flow channel 14, while collecting the same amount of emitted light from the interrogation zone 12 as a lens system 18 with more lenses in the same plane. This arrangement provides a more compact lens system 18 and detector system and therefore a smaller flow cytometer system. The lenses 18ss adapted to collect the side scatter may be placed above, below, or both above and below the common plane of the other lenses. These lenses are preferably angled 45 degrees to the common plane of the other lenses, but may alternatively define any other suitable angle. The lenses placed above (and/or alternatively below) the plane are preferably side scatter detectors, but may alternatively detect any suitable light from the interrogation zone. The additional lenses above the plane perpendicular to the flow channel 14, are preferably aligned such that their arrangement is rotated along the axis of the flow channel 14 relative to the arrangement of the lenses in the parallel plane perpendicular to the flow channel 14. The rotation is preferably rotated 45 degrees relative to the arrangement of the parallel plane perpendicular to the flow channel. This arrangement not only creates a more compact lens system 18, but also detects more light in a compact lens system and thus create a more efficient and compact flow cytometer.

Figure 6:
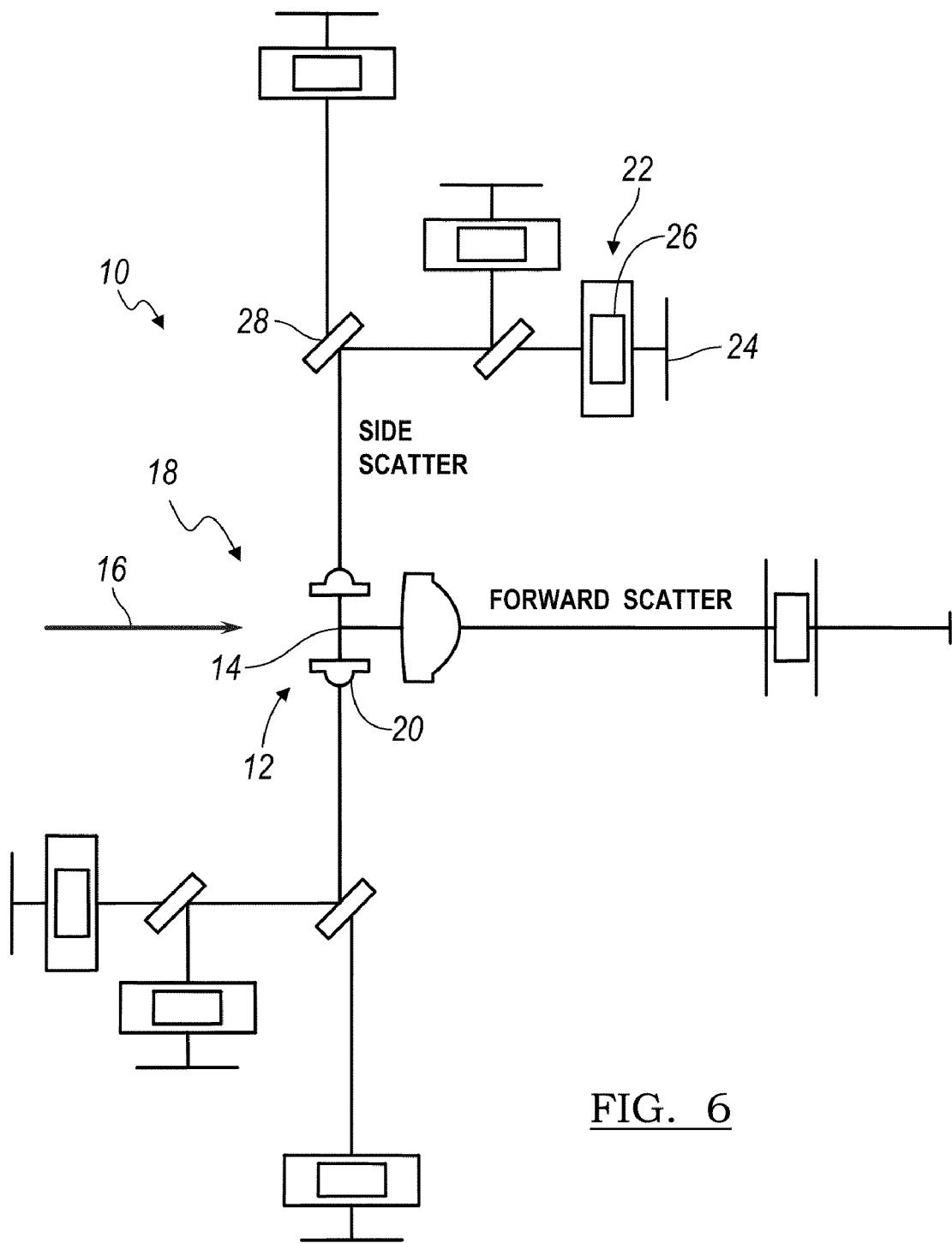
FIG. 6 is a schematic representation of a second variation of the lens and detector system arrangement of the preferred embodiment.

In a second variation of the preferred embodiment, as shown in FIG. 6, the detector system includes more detectors 24 than lens surfaces 20 of the lens system 18. In this variation, the lens system 18 also includes conventional optic devices, such as beam splitters 28, to branch the collected and directed light to the detector system. In this variation, the beam splitters 28 are preferably nonselective with regard to wavelength, which preserves the freedom to independently filter for specific wavelengths (by using local filters 26) at each of the various detectors 24. However, the beam splitter 28 may alternatively be selective with regard to wavelength.

3. Ambient Light Absorption for the Detectors

Figure 7:
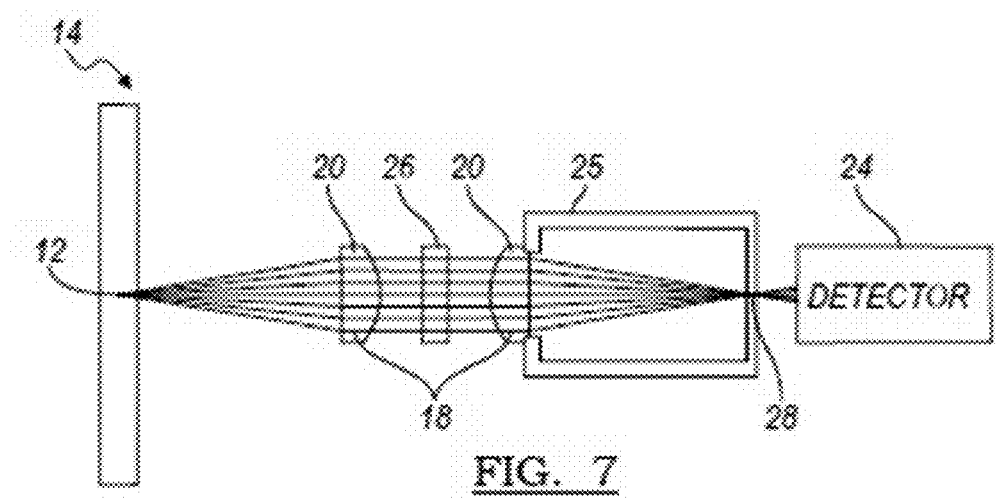
FIG. 7 is a schematic representation of the ambient light absorption of the detectors of the preferred embodiment.

As shown in FIG. 7, the some of the detectors of the preferred embodiment (such as the fluorescence detectors and, additionally or alternatively, the side scatter detectors) include at least one collimating lens 18, a local filter 26, an absorption element 25, and a detector 24 to detect light emitted from the interrogation zone 12 of a flow channel 14. The collimating lens 18 functions to collimate the light received from an interrogation zone 12 on a flow channel 14. The collimated light is then filtered by the local filter 26, and preferably decollimated by another collimating lens 18, before passing through the absorption element 25. The local filter 26 functions to filter the light by allowing certain wavelengths of light to pass through. The local filter 26 preferably absorbs the light at blocked wavelengths, however, it may reflect the blocked wavelengths of light back through the interrogation zone 12 on a flow channel 14 and into another detector system perfectly aligned with the current detector system. The absorption element 25 functions to trap and absorb any light and/or ambient that is not in the focused beam. Preferably, at one end of the absorption element 25 is a collimating lens that accepts collimated light and focuses the collimated light. More preferably, at the other end of the absorption element 25 is a hole 28 to allow the focused beam of light to pass through to a detector 24. The absorption element 25 is preferably shaped as a canister, with a large opening for a collimated lens 18 to focus collimated light and a small opening 28 for the light focused by the collimated lens 18 to exit the absorption element 25 and enter a detector 24. However, the absorption element 25 may be of any shape that allows the absorption element 25 to trap light as desired. The absorption element 25 is preferably black in color, to absorb light, but may alternatively be any color or material that will allow the absorption element 25 to absorb light. The absorption element 25 is preferably made of plastic, but may alternatively be made from any material that may allow the absorption element 25 to absorb light.

4. Retroreflectance for the Filters

Figure 8:
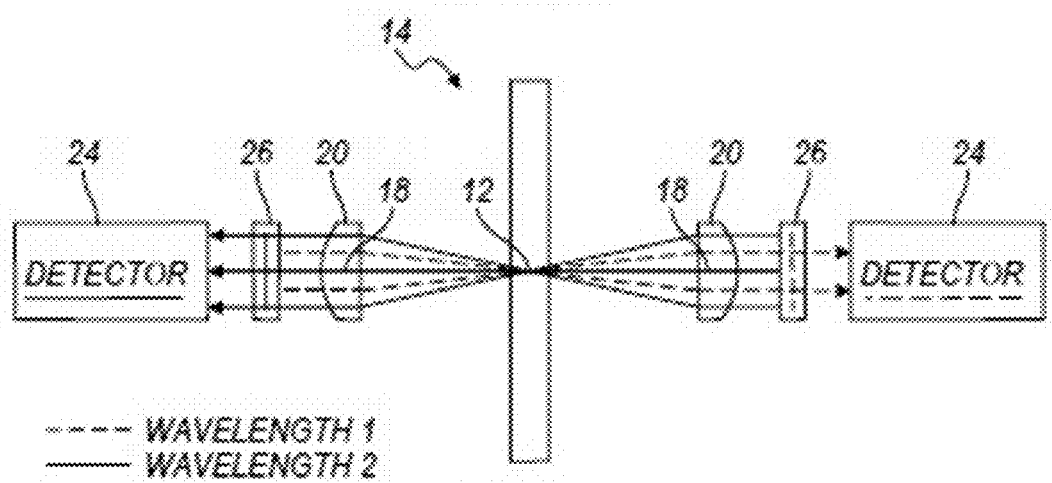
FIG. 8 is a schematic representation of the retroreflectance of the fluorescence detectors of the preferred embodiment.
Figure 10:
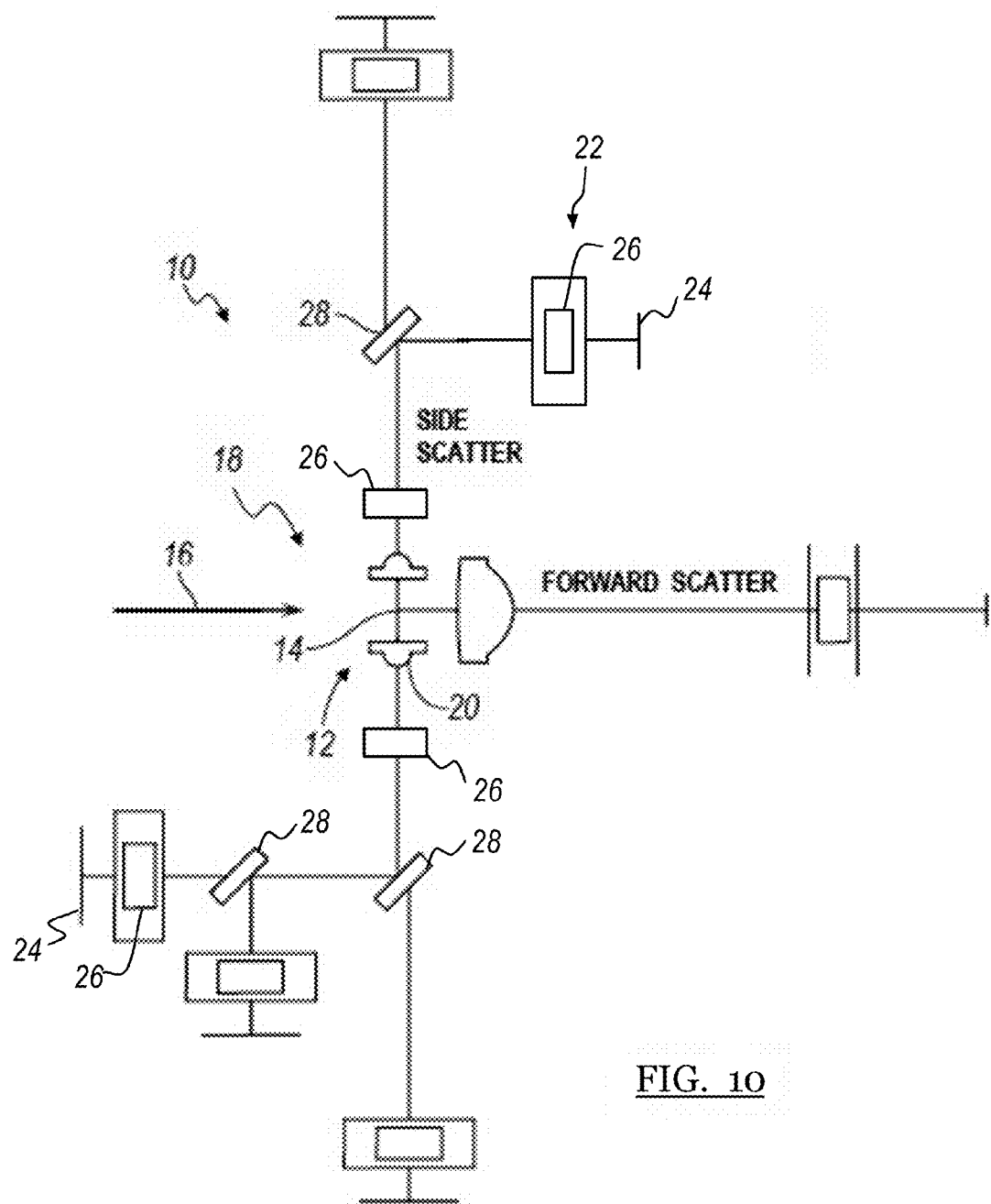
FIG. 10 is a schematic representation of another variation of the lens and detector arrangement of the preferred embodiment.

As shown in FIGS. 8 and 10, at least two of the local filters 26 of the preferred embodiment are located with a particular arrangement such that a first filter 26 absorbs a first wavelength and at least partially reflects a second wavelength, while the second filter 26 absorbs the second wavelength and at least partially reflects the first wavelength. In a first variation, the two filters are located on opposite sides of the flow channel 14 and are perfectly aligned such that the light that does not pass through one local filter 26 is reflected, either partially or entirely, back through the lens system 18, and the interrogation zone 12 of the flow channel 14, through the lens system 18, and into the other local filter 26. One or both of the two filters 26 may or may not be coupled to a detector 24 such that a first detector 24 absorbs light passing through the first filter 26 and a second detector 24 absorbs light passing through the second filter 26. The lens coatings 20 on the lenses 18 may also function to reflect and/or filter the light. The lens system 18 is preferably perfectly aligned to have a common focal point between at least two opposing lenses, which may reduce ambient light effects on the collected data. If the opposing filters 26 are perfectly aligned with each other, the reflected frequencies of light from one local filter 26 will pass through the system and into the corresponding local filter 26 on the other side, and the power of the light would significantly increase. While empirical results show that the detected power of light is improved by 40-70%, the detected power of light could theoretically double, thereby improving the signal and quality of collected data. In a second variation, two filters 26 are opposite to each other in any location relative to the flow cytometer, In a third variation, three or more filters 26 and/or detectors 24 may be arranged with appropriate lens such the light that does not pass through one local filter 26 is reflected, either partially or entirely, directly to the lens system 18, and into the other local filter 26 coupled to the detector 24.

By reflecting this light through the interrogation zone 12 of the flow channel 14, it is possible that the sample flowing through the interrogation zone 12 of the flow channel 14 may be re-excited by the reflected light as it travels through the interrogation zone 12 of the flow channel 14. This potential error is preferably minimized or eliminated by appropriate signal processing. Additionally, any reflected light that is detected will have an additional phase delay due to the extra distance traveled by the reflected light. Again, this potential error is preferably minimized or eliminated by appropriate signal processing by using—amongst other information—the distance between the lenses 18 from the center of the flow channel 14 (which is preferably about 6 mm).

In one variation, an optical system facilitating retroreflectance preferably includes, as described above, at least two lenses 18$ss$ that function to collect side scatter from the interrogation zone of the flow channel, at least two lenses 18$fl$ that function to collect fluorescence from the interrogation zone of the flow channel, and one lens 18$fs$ that functions to collect forward scatter from the interrogation zone of the flow channel. However, the lens system 18 may include any suitable number and arrangement of lenses. In this variation, the lens system 18 may include all of the lenses arranged in a common plane, or only some lenses arranged in a common plane with other lenses arranged in a different plane, as described above. The retroreflectance aspect may be facilitated between filters coupled to two or more fluorescence detectors, two or more side scatter detectors, or any combination thereof, or of any suitable detectors.

Figure 11:
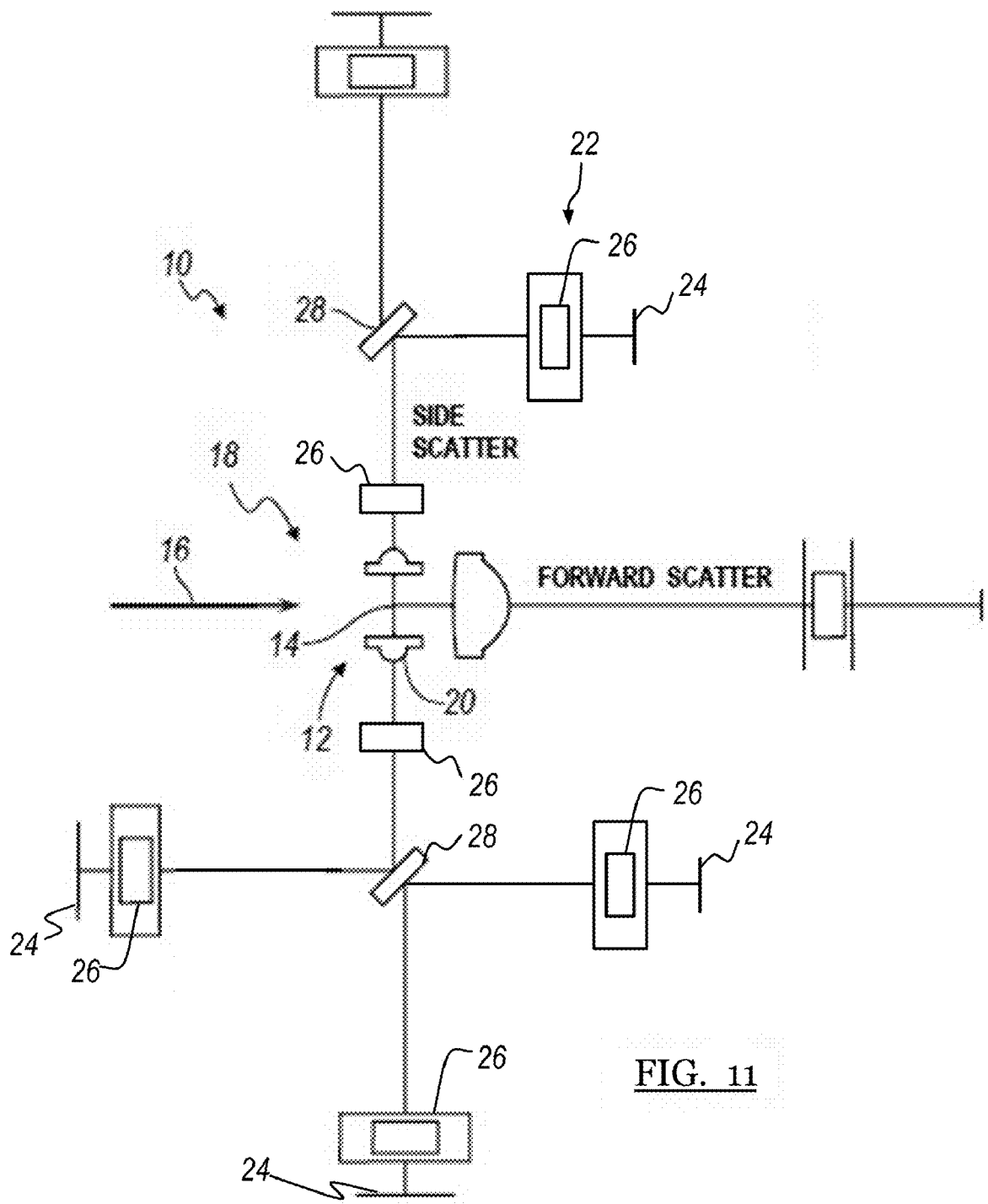
FIG. 11 is a schematic representation of another variation of the lens and detector arrangement of the preferred embodiment.

In another variation, an optical system facilitating retroreflectance includes, as described above, more detectors 24 than lens surfaces 20 of the lens system 18 and one or more beam splitters that branch collected and collimated light to one or more detectors. As shown in FIG. 10, in one embodiment, a first filter 26 allows passage of light in a first portion of a frequency band and reflects light in a second portion of the frequency band, while a second filter 26 reflects light in the first portion of the frequency band and allows passage of light in the second portion of the frequency band. A beam splitter 28 preferably branches the light in the first portion of the frequency band to at least a first detector. In a first variation, the beam splitter 28 branches the light in the first portion of the frequency band to a first detector and a second detector. In a second variation, the beam splitter 28 branches the light in the first portion of the frequency band to the first detector 24 and to a second beam splitter 28, and the second beam splitter 28 further branches the light to a second detector 24 and a third detector 24. Similarly, another beam splitter may branch the light in the second portion of the frequency band to a third detector and a fourth beam splitter and/or fourth detector. Other variations include further "branches" and/or any suitable combination and permutation of beam splitters and filters exhibiting retroreflectance. In a third variation, as shown in the bottom of FIG. 11, the beam splitter 28 also captures backreflected light (that otherwise might be lost) to another detector. In this third variation, the beam splitter 28, preferably branches approximately half of the light to a first detector and allows transmission of approximately half of the light towards a second detector (with very low loss of light, e.g. <5% of the light). The beam splitter 28 may also further branch at least a portion of backreflected light from the second detector (e.g., reflected from a filter coupled to the detector) to a third detector. This backreflected light from the second detector might otherwise be lost and/or unusable for processing.

In further variations, an optical system facilitating retroreflectance includes a combination substantially of the first and second variations, or any suitable combination and/or permutation of the first, second, and third variations. Additional features including waveguides such as fiber optic cables that direct light paths may be included, such as to enable pairs of detector 24 and/or filter 26 groups to be aligned and located opposite to each other, in any suitable orientation relative to the flow channel, to exhibit retroflectance.

5. Beam Blocker for the Forward Scatter Detector

Figure 9:
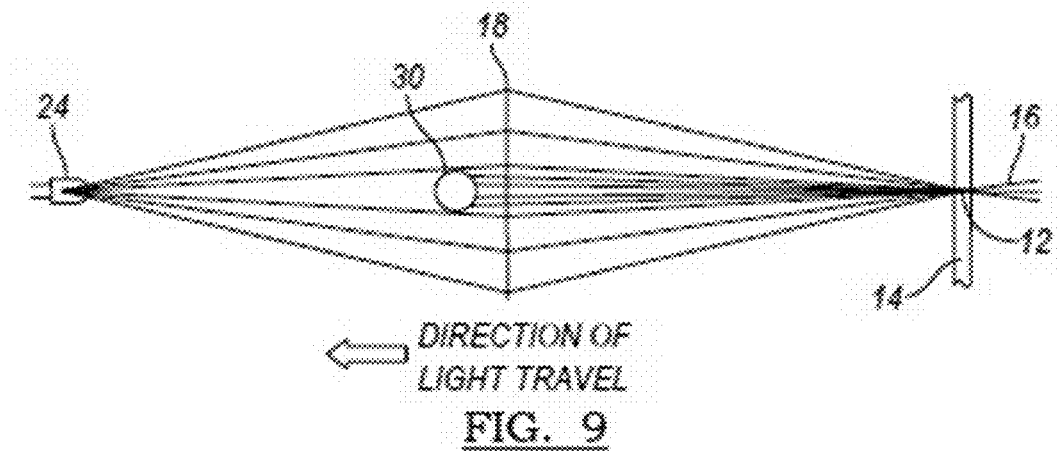
FIG. 9 is a schematic representation of the beam blocker of the forward scatter detector of the preferred embodiment.

As shown in FIG. 9, the forward detector preferably includes a beam blocker 30. The beam blocker 30 functions to reduce or block light from the illumination source (or laser beam) 16 that has passed through the interrogation zone 12 of the flow channel 14 from entering the detectors 24. In a flow cytometer, focused laser light 16 hits the target particles traveling through the interrogation zone 12 capillary 14 and light scatters off the particles in many directions. The focused laser light 16 continues on its previous path as it exits the capillary. The forward scatter detection lens 18 collects specific angles of scattered light (known as forward scatter). This light travels in the same direction as the exiting laser beam 16. The collection lens 18 focuses all the collected light on the detector 24.

The beam blocker 30 is preferably an opaque pin, and is preferably placed between at least one collection lens 18fs and at least one detector 24. The beam blocker 30 is preferably sized specifically to serve as a physical barrier to the laser beam 16 while allowing the scattered light of interest to pass above and below. The scattered light is then preferably recorded by the detector 24 while the beam blocker 30 absorbs and reflects the laser beam 16. The positioning of the beam blocker 30 between the collection lens 18 and the detector 24 takes advantage of the fact that the laser beam 16 is now converging (because of the lens 18fs) to more easily stop the beam 16. The position of the beam blocker 30 also has more tolerance in its position and is preferably not adjustable, enabling cheaper and easier manufacturing and more robust flow cytometer operation.

As a person skilled in the art will recognize from the previous detailed description and from the figures and claims, modifications and changes can be made to the preferred embodiments of the invention without departing from the scope of this invention defined in the following claims.

We claim:

1. An optical system for a flow cytometer that includes a flow channel with an interrogation zone, and an illumination source that impinges the flow channel in the interrogation zone from a particular direction, the optical system comprising:
   a lens system including at least two lens surfaces located on opposite sides of the interrogation zone of the flow channel, wherein the two lens surfaces are aimed directly at, and are configured to collect and collimate light directly from, the interrogation zone; and
   a detection system configured to detect light from the lens system, including:
   first local filter that allows passage of a first wavelength of light and at least partially reflects a second wavelength of light; and
   a second local filter that at least partially reflects of the first wavelength of light and allows passage of the second wavelength of light;
   wherein the first and second filters are aligned such that light reflected from the first filter passes through the second filter, and light reflected from the second filter passes through the first filter.

2. The optical system of claim 1, wherein the first filter and second filter are located on opposite sides of the flow channel.

3. The optical system of claim 1, wherein at least a portion of the reflected light from one or more of the filters is reflected through the lens system.

4. The optical system of claim 1, wherein the two lens surfaces share a common focal point.

5. The optical system of claim 4, wherein at least one of the detectors performs signal processing on the reflected light.

6. The optical system of claim 4, wherein the detection system further includes a first detector and a second detector, wherein the first detector absorbs light passing through the first filter and the second detector absorbs light passing through the second filter.

7. The optical system of claim 6, wherein at least one of the first and second detectors performs signal processing to remove phase delay on the reflected light.

8. The optical system of claim 6, wherein the detection system further includes a third detector and a third local filter that are arranged relative to the lens surfaces such that light at least partially reflected from one local filter passes through another local filter and into another detector.

9. The optical system of claim 1, wherein at least one of the lens surfaces includes a coating that converts the lens surface to a wavelength-specific filter.

10. The optical system of claim 1, wherein the lens system includes a unitary piece with multiple facets defining the lens surfaces.

11. The optical system of claim 1, wherein the lens system includes multiple lenses.

12. The optical system of claim 1, wherein at least one of the local filters is swappable with another local filter.

13. The optical system of claim 1, wherein the lens system includes three or more lens surfaces arranged around the interrogation zone of the flow channel and aimed directly at, and configured to collect and collimate light directly from, the interrogation zone.

14. The optical system of claim 13, wherein the detector system includes a detector for each lens surface of the lens system, and each detector is arranged in a direct, unbranched light path from a corresponding lens surface.

15. The optical system of claim 13, wherein at least a portion of the lens surfaces are arranged in a first plane and configured to collect fluorescence from the interrogation zone of the flow channel, and wherein at least one of the first and second detectors are fluorescence detectors that are configured to absorb the fluorescence.

16. The optical system of claim 15, wherein a portion of the lens surfaces are arranged outside of the first plane and configured to collect side scatter from the interrogation zone of the flow channel, wherein at least one of the first and second detectors are side scatter detectors that are configured to absorb the side scatter.

17. The optical system of claim 16, wherein at least one of the side scatter detectors is in a second plane angled approximately 45 degrees relative to the first plane.

18. The optical system of claim 1, wherein the detector system includes multiple detectors for each lens surface of the lens system.

19. The optical system of claim 18, further comprising a beam splitter that branches the collected and collimated light from the lens surface to the multiple detectors.

20. The optical system of claim 19, wherein the beam splitter is nonselective with respect to wavelength.

21. The optical system of claim 19, wherein:
   the first local filter allows passage of light in a first portion of a frequency band and reflects light in a second portion of the frequency band;
   the second local filter reflects light in the first portion of the frequency band, and allows passage of light in the second portion of the frequency band; and
   the beam splitter branches the light in the first portion of the frequency band to a first detector.

22. The optical system of claim 21, wherein the beam splitter branches the light in the first portion of the frequency band to the first detector and a second detector.

23. The optical system of claim 22, further comprising a second beam splitter that branches the light in the second portion of the frequency band to a third detector and a fourth detector.

24. The optical system of claim 21, further comprising a second beam splitter, wherein the first beam splitter branches the light to the first detector and to the second beam splitter, and wherein the second beam splitter further branches the light to a second detector and a third detector.

* * * * *

UNITED STATES PATENT AND TRADEMARK OFFICE
CERTIFICATE OF CORRECTION

| | | |
|---|---|---|
| PATENT NO. | : 8,031,340 B2 | Page 1 of 1 |
| APPLICATION NO. | : 12/887392 | |
| DATED | : October 4, 2011 | |
| INVENTOR(S) | : Rich et al. | |

It is certified that error appears in the above-identified patent and that said Letters Patent is hereby corrected as shown below:

In column 7, line 52, "partially reflects of the" should read --partially reflects the--

Signed and Sealed this
Twenty-second Day of November, 2011

David J. Kappos
*Director of the United States Patent and Trademark Office*